United States Patent
Maro et al.

(10) Patent No.: US 10,234,362 B2
(45) Date of Patent: Mar. 19, 2019

(54) DEVICE FOR SEQUENTIALLY COLLECTING RAINWATER, IN PARTICULAR WITH A VIEW TO STUDYING THE VARIATION IN THE RADIOACTIVITY OF RAINWATER

(71) Applicant: INSTITUT DE RADIOPROTECTION ET DE SURETE NUCLEAIRE, Fontenay aux Roses (FR)

(72) Inventors: Denis Maro, Cherbourg-Octeville (FR); Philippe Laguionie, Valognes (FR)

(73) Assignee: INSTITUT DE RADIOPROTECTION ET DE SURETE NUCLEAIRE, Fontenay aux Roses (FR)

( * ) Notice: Subject to any disclaimer, the term of this patent is extended or adjusted under 35 U.S.C. 154(b) by 193 days.

(21) Appl. No.: 15/505,467

(22) PCT Filed: Aug. 18, 2015

(86) PCT No.: PCT/EP2015/068908
§ 371 (c)(1),
(2) Date: Jun. 21, 2017

(87) PCT Pub. No.: WO2016/026836
PCT Pub. Date: Feb. 25, 2016

(65) Prior Publication Data
US 2018/0045617 A1    Feb. 15, 2018

(30) Foreign Application Priority Data
Aug. 22, 2014 (FR) .................................. 14 57941

(51) Int. Cl.
*G01N 1/18* (2006.01)
*G01W 1/14* (2006.01)
(Continued)

(52) U.S. Cl.
CPC ................ *G01N 1/18* (2013.01); *G01W 1/14* (2013.01); *E03B 3/03* (2013.01); *G01N 33/18* (2013.01); *Y02A 20/106* (2018.01)

(58) Field of Classification Search
CPC ........... G01N 1/18; G01N 33/18; G01W 1/14; Y02A 20/106; E03B 3/03
See application file for complete search history.

(56) References Cited

U.S. PATENT DOCUMENTS 6,264,832 B1    7/2001   Panahi

FOREIGN PATENT DOCUMENTS

| EP | 0 656 448 | 6/1995 |
| FR | 2 912 162 | 8/2008 |
| WO | WO-2009/044927 | 4/2009 |

OTHER PUBLICATIONS

International Search Report dated Oct. 30, 2015 in PCT/EP2015/068908.

*Primary Examiner* — Jason K Niesz
(74) *Attorney, Agent, or Firm* — B. Aaron Schulman, Esq.; Stites & Harbison, PLLC

(57) ABSTRACT

The invention relates to a collection device (10) that comprises a plurality of collection containers (12A, 12B, 12C) suitable for receiving rainwater, each collection container (12A. 12B, 12C) comprising a circumferential wall (14) and a lower wall (16). The collection containers (12A, 12B, 12C) are stacked so as to form a stack along a vertical axis (Z). Each container (12A, 12B) arranged above another, adjacent container (12B, 12C) comprises a water flow opening (18) that is provided in the lower wall (16) thereof and leads into said other, adjacent container (12B, 12C). Each container (12B, 12C) that is arranged below another, adjacent container (12A, 12B) houses a buoyant closure element (20) that is movable along the vertical axis (Z) between a lower position and an upper position depending on the amount of (Continued)

water in said container (12B, 12C) and closes the flow opening (18) in the upper position.

12 Claims, 1 Drawing Sheet

(51) Int. Cl.
*E03B 3/03* (2006.01)
*G01N 33/18* (2006.01)

DEVICE FOR SEQUENTIALLY COLLECTING RAINWATER, IN PARTICULAR WITH A VIEW TO STUDYING THE VARIATION IN THE RADIOACTIVITY OF RAINWATER

The present invention relates to a device for sequentially collecting rainwater, notably with view to studying the variation in the radioactivity of rainwater.

In the state of the art, a collecting device including a receptacle of large dimensions, is already known which gradually fills up according to rains. Since all the rainwaters are collected in a same receptacle, such a collecting device does not give the possibility of studying a variation in the activity of rainwater overtime.

In order to study this variation, in the state of the art a collecting device is also known a so called sequential collecting device, including a plurality of receptacles of collections intended to receive rainwater, these receptacles may be open or closed independently. However, such a collecting device is particularly expensive, and it requires a source of energy for powering means for opening and closing the receptacles. This energy is generally electricity delivered on and by an electric network, so that such a collecting device has constraints related to its connection with this electric network, which limit its possibilities of installation in the environment.

The object of the invention has notably the goal of finding a remedy to these drawbacks, by providing a rainwater collecting device of the sequential type not requiring any energy source, while remaining economical.

For this purpose, the object of the invention is notably a rainwater collecting device, including a plurality of collecting receptacles intended to receive rainwater, each collecting receptacle including a circumferential wall and a lower wall, characterized in that:

the collecting receptacles are stacked, forming a stack along a vertical axis, each receptacle arranged above another adjacent receptacle includes an aperture for water flow made in its lower wall, this flow aperture opening into this other adjacent receptacle, each receptacle arranged above another adjacent receptacle houses a floating obturation element, movable along the vertical axis between a low position and a high position depending on the amount of water in this receptacle, the obturation element having a shape complementary of that of the water flow aperture of the adjacent receptacle arranged below, obturating this flow aperture in the high position, and each receptacle housing an obturation element includes magnetic means for maintaining the obturation element in a high position.

As the collecting receptacles are stacked, rainwater flow through these receptacles, notably through the flow apertures, as far as an inner receptacle arranged at the lowest position. Gradually as this lower receptacle is filled, the floating obturation element housed in this receptacle is moved from its low position as far as its high position. In the high position, the flow aperture opening into this lower receptacle is obturated, and rainwater now fills a new receptacle. Thus, in the long run, the receptacles include rain waters corresponding to different precipitations, which do not mix.

It therefore clearly appears that the collecting device according to the invention gives the possibility of studying the time-dependent change of the rainwater condition.

The closing of the receptacles being made in a mechanical way, by the floating obturation elements, the collecting device according to the invention does not require any powering source.

Finally, the collecting device according to the invention has a simple structure and is therefore particularly economical.

A collecting device according to the invention may further include one or several of the following features, taken alone or according to all the technically conceivable combinations.

The plurality of receptacles include: an upper receptacle, arranged at the top of the stack, for which the lower wall includes a flow aperture, a lower receptacle, arranged at the bottom of the stack, housing an obturation element, and at least one intermediate receptacle, arranged between the upper receptacle and the lower receptacle in the direction of the vertical axis, having a lower wall on the one hand including a flow aperture and housing on the other hand a floating obturation element.

The receptacles are assembled in a detachable way with each other, for example by screwing or snap-fastening.

Each receptacle includes an emptying channel crossing its circumferential wall in proximity to its lower wall, each emptying channel being provided with a valve.

The lower wall of each receptacle has a concavity, into which opens the emptying channel of this receptacle.

A seal gasket is arranged between each obturation element and each complementary flow aperture, the seal gasket being borne by the obturation element or by a perimeter of the flow aperture.

The magnetic means include an annular element, housed in the receptacle in proximity to the lower wall of the adjacent receptacle located immediately above, one from among the annular element and the obturation element being in a magnetic material and the other in a ferromagnetic material.

Each obturation element has a cone shape, and each receptacle housing an obturation element has an element having a frusto-conical aperture for receiving the obturation element in the high position.

The plurality of receptacles includes an upper receptacle, arranged at the top of the stack, comprising a channel for discharging overflow crossing its circumferential wall at an upper end of this upper receptacle.

The invention will be better understood upon reading the description which follows, only given as an example and made with reference to the appended figures wherein.

Figure 1:
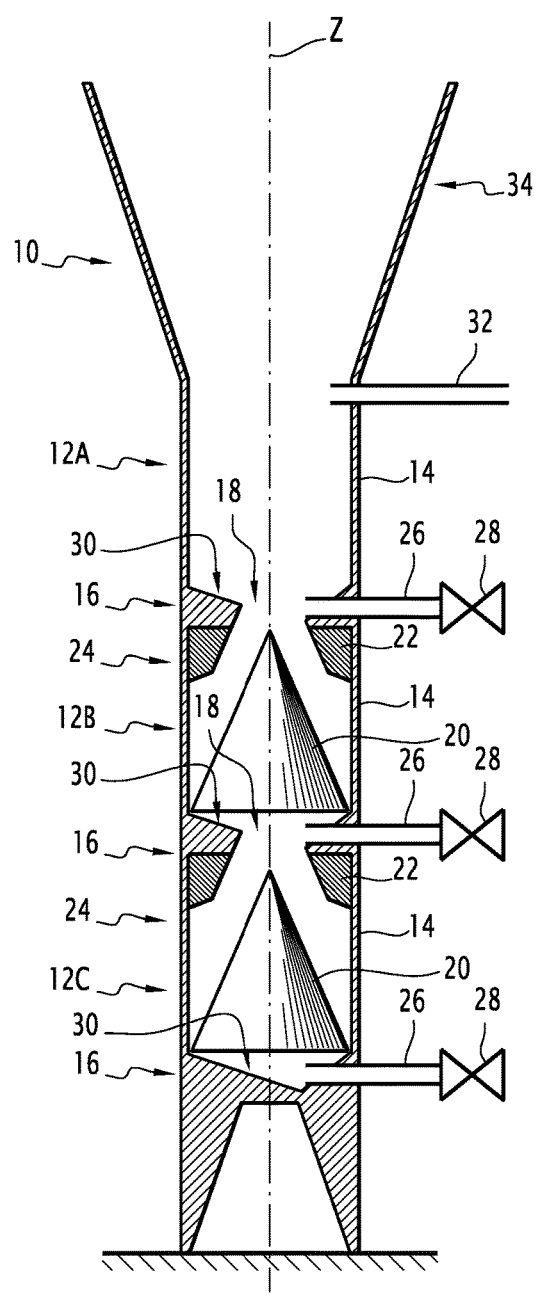
FIG. 1 is a schematic sectional view of a device for collecting rainwater according to an exemplary embodiment of the invention, wherein the collecting receptacles are open.

In FIG. 1, a rainwater collecting device 10 is illustrated according to an exemplary embodiment of the invention.

The collecting device 10 includes a plurality of receptacles 12A, 12B, 12C, intended to receive rainwater. Each collecting receptacle 12A, 12B, 12C includes a circumferential wall 14, and a lower wall 16. Each collecting receptacle 12A, 12B, 12C for example has a general cylindrical shape with a circular section, extending along an axis Z.

The collecting receptacles 12A, 12B, 12C are stacked so as to form a stack along the Z axis. The axis Z in the present description will be called a "vertical axis" since, for a normal use of the collecting device 10, the collecting receptacles 12A, 12B, 12C should be stacked vertically.

In the present description, the terms of "upper", "lower", "above", "below", "high" and "low" are defined along this vertical axis Z, with their standard direction.

In the illustrated example, the plurality of receptacles 12A, 12B, 12C includes an upper receptacle 12A, arranged at the top of the stack, an intermediate receptacle 12B, and a lower receptacle 12C, arranged at the bottom of the stack. The intermediate receptacle 12B is therefore arranged between the upper receptacle 12A and the lower receptacle 12C in the direction of the vertical axis Z.

According to an alternative not shown, the stack may include at least two intermediate receptacles 12B, identical, stacked between the upper receptacle 12A and the lower receptacle 12C.

According to another alternative not shown, the stack may not include any intermediate receptacle 12B, but only an upper receptacle 12A and a lower receptacle 12C.

More particularly, the number of receptacles is selected according to the number of samples of rainwater which one desires to carry out.

Advantageously, the receptacles 12A, 12B, 12C are assembled in a detachable way with each other, for example by screwing or snap-fastening. Each receptacle 12A, 12B, 12C therefore forms a module, so that the collecting device 10 is modular and may have in a simple way a desired number of receptacles.

In order to allow flow of the rain waters as far as the lower receptacle 12C, each receptacle 12A, 12B arranged above another adjacent receptacle 12B, 12C includes an aperture 18 for flow of water made in its lower wall 16, this flow aperture 18 opening into said other adjacent receptacle 12B, 12C. More particularly, the upper receptacle 12A, as well as each intermediate receptacle 12B, includes such a flow aperture 18 in its lower wall 16.

On the other hand, the lower receptacle 12C does not include any flow aperture in its lower wall 16. Alternatively, the lower receptacle 12C has a structure identical with that of the intermediate receptacle 12B, in which case its flow aperture 18 is obturated, for example with a base on which is positioned this lower receptacle 12C.

Figure 2:
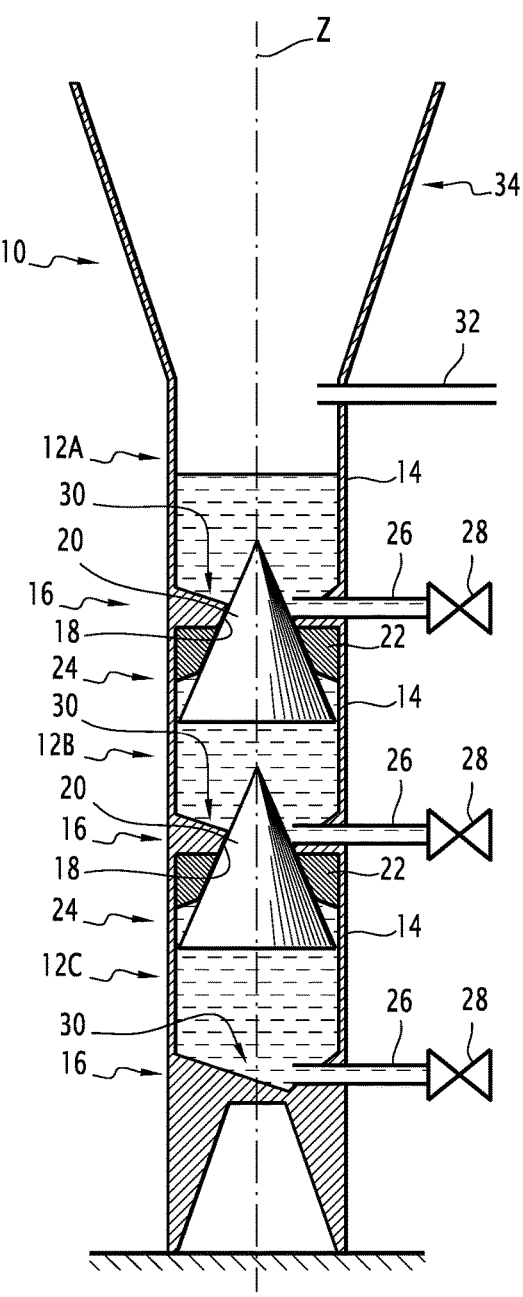
FIG. 2 is a schematic sectional view of a detail of the collecting device of FIG. 1, illustrating a closed collecting receptacle.

Moreover, each receptacle 12B, 12C arranged below another adjacent receptacle 12A, 12B houses a floating obturation element 20. This floating obturation element 20 is movable along the vertical axis Z between a low position and a high position, depending on the amount of water in this receptacle 12B, 12C. The obturation element 20 has a shape mating that of the water flow aperture 18 of the adjacent receptacle 12A, 12B directly arranged above, so that it may obturate this flow aperture 18 when it is found in the high position, as this is illustrated in FIG. 2.

On the other hand, the obturation element 20 has a shape allowing flow of water towards the adjacent receptacle 12B, 12C arranged below when it is found in its low position. For this purpose, the obturation element 20 may have grooves for the passing of water into its low portion, having legs over raising the obturation element 20 in a low position, or having any other conceivable means for allowing flow of the water.

Advantageously, the collecting device 10 includes means for guiding in translation each obturation element 20 along the vertical axis Z. These guiding means may assume any conceivable shape.

For example, in the example illustrated, each obturation element 20 has a cone shape, and each receptacle 12B, 12C housing such an obturation element 20 has an annular element 22, having a frusto-conical aperture for guiding the obturation element 20 and for receiving this obturation element 20 in a high position. This annular element 22 allows both guiding the obturation element 20 when it is displaced towards its high position and of optimizing the seal between both adjacent receptacles, by increasing the contact surface between the obturation element 20 with a cone shape and the annular element 22.

Advantageously, a seal gasket (not shown) is arranged between each obturation element 20 and each complementary flow aperture 18. The seal gasket is for example borne by the obturation element 20, or alternatively by a perimeter of the flow aperture 18, for example by the annular element 22.

According to an advantageous alternative, each receptacle 12B, 12C housing an obturation element 20 includes magnetic means for maintaining the obturation element 20 in a high position, ensuring the maintaining of the closure of this receptacle 12B, 12C.

The magnetic means 24 for example includes a maintaining element, housed in the receptacle 12B, 12C in proximity to the lower wall of the adjacent receptacle located just above, one from among the maintaining element and the obturation element 20 being in a magnetic material, and the other one in a ferromagnetic material.

In the illustrated example, the maintaining element is formed by the annular element 22.

For example, the obturation element 20 is in non-stainless steel, covered with a polymer protecting the steel from roughed.

It clearly appears that the lowest receptacle which is not yet filled, is gradually filled with the rainwater flowing into the receptacles, causing the rise of its obturation element 20 as far as its high position. Once this high position is reached, this obturation element 20 obturates the flow aperture opening into this receptacle, so that this receptacle is thus closed and isolated from the other receptacles. This is then the receptacle immediately above which will be filled in the same way.

The receptacles are therefore filled gradually, one after the other, until the upper receptacle 12A is also full.

Since the receptacles are filled one after the other, they include rain waters corresponding to different precipitations, which allows observation of a variation in the condition of the rainwater.

Optionally, the water collecting device 10 is associated with a weather station (not shown), which notes the precipitations and therefore allows inference of the dates of the precipitations corresponding to the different samplings.

In order to sample water from each receptacle 12A, 12B, 12C, each receptacle includes an emptying channel 26 crossing its circumferential wall 14 in proximity to its lower wall 16. Each emptying channel 26 is provided with a valve 28, which is closed during the collection of rainwater, and open during a sampling of the water from the corresponding receptacle.

Advantageously, each lower wall 16 has a concavity 30, into which opens the emptying channel 26. This concavity 30 gives the possibility of driving the water towards the emptying channel 26, in order to ensure that all the water of the receptacle is properly discharged through the emptying channel 26.

Once the rainwater is sampled, the latter is analyzed in a way known per se.

Optionally, the upper receptacle 12A comprises a channel for discharging overflow 32, crossing its circumferential wall 14 at an upper end of this upper receptacle 12A. Thus, the upper receptacle 12A cannot be filled beyond this discharge channel 32

Finally, the collection device 10 advantageously includes an inlet cone 34, arranged above the upper receptacle 12A, facilitating entry of the rain waters into the collecting device 10.

It will be noted that the invention is not limited to the embodiment described earlier, but may have diverse alternatives.

In particular, each obturation element may have a different shape from the one described earlier.

The invention claimed is:

1. A collecting device for collecting rainwater, including a plurality of collecting receptacles intended to receive rainwater, each collecting receptacle including a circumferential wall and a lower wall, wherein:
    the collecting receptacles are stacked, forming a stack along a vertical axis,
    each collecting receptacle that is arranged above another adjacent lower collecting receptacle includes a flow aperture for water flow made in its lower wall, this flow aperture opening into this other adjacent lower collecting receptacle,
    each collecting receptacle that is arranged below another adjacent upper collecting receptacle houses a floating obturation element, movable along the vertical axis between a low position and a high position depending on the amount of water in said collecting receptacle arranged bellow, the obturation element having a shape mating that of the flow aperture of the adjacent upper collecting receptacle arranged above, obturating this flow aperture in the high position, and
    wherein each collecting receptacle housing an obturation element includes magnetic maintainers configured for maintaining the obturation element in the high position.

2. The collecting device according to claim 1, wherein the plurality of collecting receptacles includes:
    top collecting receptacle, arranged at the top of the stack, the lower wall of which includes a flow aperture,
    a bottom collecting receptacle, arranged at the bottom of the stack, housing an obturation element, and
    at least one intermediate collecting receptacle, arranged between the top collecting receptacle and the bottom collecting receptacle in the direction of the vertical axis, having on the one hand a lower wall including a flow aperture and housing on the other hand a floating obturation element.

3. The collecting device according to claim 1, wherein the collecting receptacles are assembled in a detachable way to each other.

4. The collecting device according to claim 1, wherein each collecting receptacle includes an emptying channel crossing its circumferential wall in proximity to its lower wall, each emptying channel being provided with a valve.

5. The collecting device according to claim 4, wherein the lower wall of each collecting receptacle has a concavity, into which opens the emptying channel of this collecting receptacle.

6. The collecting device according to claim 1, wherein a seal gasket is arranged between each obturation element and each complementary flow aperture, the seal gasket being borne by the obturation element.

7. The collecting device according to claim 1, wherein the magnetic maintainers include an annular element, housed in the collecting receptacle in proximity to the lower wall of the adjacent upper collecting, receptacle located immediately above, one from among the annular element and the obturation element being in a magnetic material and the other one in a ferromagnetic material.

8. The collecting device according to claim 1, wherein each obturation element has a cone shape, and each collecting receptacle housing an obturation element has an element having a frusto-conical aperture for receiving the obturation element in the high position.

9. The collecting device according to claim 1, wherein the plurality of collecting receptacles includes a top collecting receptacle, arranged at the top of the stack, comprising a channel for discharging an overflow crossing its circumferential wall at an upper end of this top collecting receptacle.

10. The collecting device according to claim 3, wherein the collecting receptacles are assembled by screwing.

11. The collecting device according to claim 3, wherein the collecting receptacles are assembled by snap fastening.

12. The collecting device according to claim 1, wherein a seal gasket is arranged between each obturation element and each complementary flow aperture, the seal gasket being borne by a perimeter of the flow aperture.

\* \* \* \* \*